United States Patent [19]

Worland

[11] Patent Number: 4,986,833
[45] Date of Patent: Jan. 22, 1991

[54] GLENOID COMPONENT FOR AN ARTIFICIAL SHOULDER JOINT

[76] Inventor: Richard L. Worland, 8721 Ruggles Rd., Richmond, Va. 23229

[21] Appl. No.: 347,866

[22] Filed: May 5, 1989

[51] Int. Cl.$^5$ .............................................. A61F 2/40
[52] U.S. Cl. ...................................................... 623/19
[58] Field of Search ........................ 623/16, 18, 19, 22, 623/23

[56] References Cited

U.S. PATENT DOCUMENTS

| | | | |
|---|---|---|---|
| D. 285,968 | 9/1986 | Kinnett | 623/19 |
| D. 285,969 | 9/1986 | Kinnett | 623/19 |
| 3,528,109 | 9/1970 | Scales | 623/19 |
| 3,694,820 | 10/1972 | Scales et al. | 623/19 |
| 3,803,641 | 4/1974 | Golyakhovsky | 623/19 |
| 3,840,904 | 10/1974 | Tronzo | 623/22 |
| 3,842,442 | 10/1974 | Kolbel | 623/19 |
| 3,891,998 | 7/1975 | Lennox | 623/19 |
| 3,978,528 | 9/1976 | Crep | 623/19 |
| 3,979,778 | 9/1976 | Stroot | 623/19 |
| 4,040,131 | 8/1977 | Gristina | 623/19 |
| 4,045,826 | 9/1977 | Stroot | 623/19 |
| 4,206,517 | 6/1980 | Pappas et al. | 623/19 |
| 4,261,062 | 4/1981 | Amstutz et al. | 623/19 |
| 4,550,450 | 11/1985 | Kinnett | 623/19 |
| 4,676,798 | 6/1987 | Noiles | 623/19 |
| 4,693,723 | 9/1987 | Gabard | 623/19 |
| 4,865,605 | 12/1989 | Dines et al. | 623/19 |

FOREIGN PATENT DOCUMENTS

| | | | |
|---|---|---|---|
| 2579454 | 10/1986 | France | 623/19 |
| 1362187 | 7/1974 | United Kingdom | 623/19 |

Primary Examiner—David J. Isabella
Attorney, Agent, or Firm—Barnes & Thornburg

[57] ABSTRACT

A glenoid component for an artificial shoulder joint has a retainer having an ultra high molecular weight polyethylene insert affixed thereto. The insert has a concave humerally facing articulating surface on which a ball of the humeral component articulates. The insert also has a fixation tab extending through a slot in the retainer and posteriorly from a scapular facing side of the glenoid component at an oblique angle to the articulating surface. The tab is cemented to the scapula to provide short term fixation of the glenoid component to the scapula. The retainer has a plurality of porous metal coated posts extending posteriorly from the scapular side of the glenoid component at generally the same oblique angle to the articulating surface as the insert's tab. The porous metal coating on the posts promote bone ingrowth therein for long term fixation of the glenoid component to the scapula. The retainer is illustratively made from porous metal coated Ti-6Al-4V. Since the posts and tab extend posteriorly from the scapular side of the glenoid component at an angle thereto, illustratively, at an oblique angle to the articulating surface, the glenoid component can be implanted anteriorly as opposed to laterally. This reduces the amount of exposure and dislocation of the shoulder needed when the glenoid component is implanted.

5 Claims, 2 Drawing Sheets

GLENOID COMPONENT FOR AN ARTIFICIAL SHOULDER JOINT

BACKGROUND AND SUMMARY OF THE INVENTION

This invention relates to artificial shoulder joints and more particularly to the glenoid component of an artificial shoulder joint.

Total shoulder arthroplasty is the replacement of the natural shoulder joint with an artificial one. Such an artificial shoulder joint will typically have a humeral component and a glenoid component. One of the humeral and glenoid components will typically have a ball and the other component will have a concave bearing surface against which the ball articulates and which comprises an articulating surface of the artificial shoulder joint. This concave bearing surface can be part of a socket which receives the ball although it can also be less than a full socket. In many cases, the humeral component will be a ball and stem where the stem is implanted in the humerus and the glenoid component will have the concave bearing surface.

When an artificial shoulder joint is implanted during total shoulder arthroplasty, the shoulder must be exposed and dislocated to some degree to provide sufficient room to permit the components of the artificial shoulder to be implanted. The amount of exposure and dislocation required is determined by the shape of the artificial shoulder joint components and the way in which they are implanted. However, the greater the degree of shoulder exposure and dislocation, the greater the trauma to the patient. It is therefore desirable to keep the amount of exposure and dislocation to a minimum.

In the past, many glenoid components for artificial shoulder joints have been implanted laterally. However, lateral implantation requires a significantly greater degree of exposure and dislocation than would be required if the glenoid component could be implanted anteriorly.

It is an object of this invention to provide a glenoid component for an artificial shoulder joint which can be implanted anteriorly to reduce the amount of exposure and dislocation required when the glenoid component is implanted.

It is another object of this invention to provide an artificial shoulder joint where the humeral component and glenoid component are adapted for use with orienting members to facilitate orientation of the humeral component with the glenoid component.

A glenoid component for an artificial shoulder joint constructed according to this invention has a retainer having an ultra high molecular weight polyethylene insert affixed thereto. The insert has a concave humerally facing articulating surface on which a ball of the humeral component articulates. The insert also has a fixation tab extending through a slot in the retainer and posteriorly from a scapular facing side of the glenoid component at an oblique angle to the articulating surface. The tab is cemented to the scapula to provide short term fixation of the glenoid component to the scapula. The retainer has a plurality of porous metal coated posts extending posteriorly from the scapular side of the glenoid component at generally the same oblique angle to the articulating surface as the insert's tab. The porous metal coating on the posts promote bone ingrowth therein for long term fixation of the glenoid component to the scapula. Since the posts and tab extend posteriorly from the scapular side of the glenoid component at an angle thereto, illustratively, at an oblique angle to the articulating surface, the glenoid component can be implanted anteriorly as opposed to laterally. This reduces the amount that the shoulder must be exposed and dislocated when the glenoid component is implanted.

The glenoid component can also include a plurality of opposed holes in its anterior facing surface for receiving posts of a glenoid positioner. The glenoid positioner has a handle with a T-head at a distal end thereof. The posts extend axially from opposed ends of the T-head. The glenoid component is held on the glenoid positioner by the posts of the glenoid positioner being received in the opposed holes in the anterior facing surface of the glenoid component. The glenoid positioner is used to manipulate the glenoid component and properly position it in the wound when it is being implanted.

The glenoid positioner is also used in conjunction with a control wire to properly position the humeral component before the humeral component is fully inserted into the canal in the humerus. The humeral component has a hole extending transversely through a proximal end from which the tapered post which receives the ball extends. A control wire is inserted into this hole and the glenoid positioner then reinserted into the glenoid component which has at this time been affixed to the scapula of the shoulder. The humeral component is then rotated so that the control wire is at approximately a desired angle to the handle of the glenoid positioner. The humeral component is then fully seated. The cooperation of the control wire with the handle of the glenoid positioner provides a better reference for determining when the humeral component is oriented properly with respect to the glenoid component.

Additional features and advantages of the invention will become apparent to those skilled in the art upon consideration of the following detailed description of a preferred embodiment, exemplifying the best mode of carrying out the invention as presently perceived. The detailed description particularly refers to the accompanying figures in which:

DETAILED DESCRIPTION OF THE DRAWINGS

Figures 5, 6:
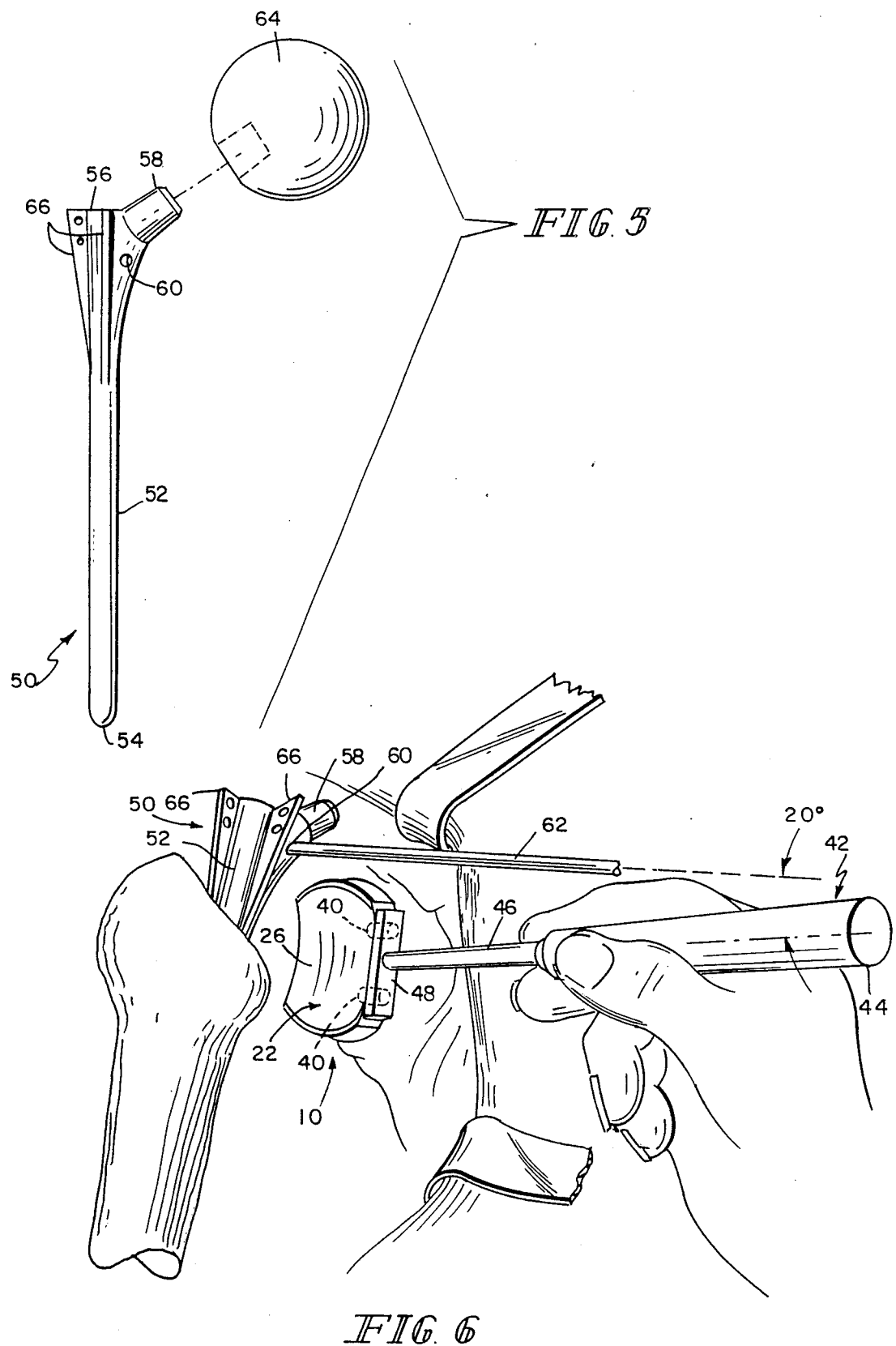
FIG. 5 is a side perspective view of a humeral component.
FIG. 6 is a perspective view of a shoulder in which the humeral component is being inserted into the humeral canal after being positioned by the use of the glenoid positioner and control wire according to this invention.

Referring to the drawings, a glenoid component 10 constructed according to this invention is shown. Glenoid component 10 is a component of an artificial shoulder joint and is used to replace the glenoid surface in total shoulder arthroplasty. Typically, the artificial shoulder joint also has a humeral component (FIG. 5).

Glenoid component 10 will be described as it is oriented when implanted in a patient's shoulder. For the purposes of this description, anterior means the front of the patient's shoulder and posterior means the back of the patient's shoulder.

Glenoid component 10 comprises a generally rectangular pad 12 formed by a retainer 14 to which an insert 16 is affixed. Glenoid component 10 has an anterior side 18, a posterior side 20, a humeral facing side 22 and a scapular facing side 24. When glenoid component 10 is implanted, it is affixed to the scapula such that insert 16 is adjacent the humerus and retainer 12 is adjacent the scapula.

The ball of the humeral component (not shown) articulates on insert 16. Insert 16 has a concave outer surface which provides an articulating surface 26 on which the ball 64 (FIG. 5) of the humeral component 50 articulates.

Retainer 14 and insert 16 also include fixation members for affixing the glenoid component 10 to the scapula. These fixation members include a plurality of posts 28, 30 of retainer 14 and a tab or fin 32 of insert 16. Posts 28, 30 of retainer 14 extend posteriorly from the scapular side 24 of glenoid component 10 at an angle thereto, illustratively, at an oblique angle to articulating surface 26. Tab 32 extends from insert 16 through an elongated slot 34 in retainer 14 also posteriorly from the scapular side 24 of glenoid component 10 and also, illustratively, at an oblique angle to articulating surface 26. The oblique angles at which posts 28, 30 and tab 32 extend are illustratively substantially the same. Importantly, by extending posteriorly from scapular side 24 of glenoid component 10 at an angle thereto, posts 28, 30 and tab 32 permit glenoid component 10 to be implanted anteriorly as opposed to laterally thus requiring less exposure and dislocation of the shoulder than if implanted laterally.

Posts 28, 30 provide for long term or permanent fixation of glenoid component 10 to the scapula. Retainer 14, including posts 28, 30, is illustratively formed from porous metal coated Ti-6A1-4V. The porous metal coating on posts 28, 30 promotes bone ingrowth therein to provide for long term or permanent fixation of glenoid component 10 to the scapula.

Insert 16, including tab 32, is illustratively formed from ultra high molecular density polyethylene and press-fitted to retainer 14. Tab 32 is cemented to the scapula to provide for short term or temporary fixation of glenoid component 10 to the scapula. Tab 32 has a hole 36 extending therethrough to facilitate the cementing of tab 32 to the scapula. When cement is applied to tab 32, it will flow through hole 36 so that both sides of tab 32 are cemented to the scapula.

The anterior facing surface 18 of glenoid component 10 can also have a plurality of positioner holes 38 extending therein. Illustratively, the holes are formed in insert 16 when insert 16 is molded. Positioner holes 38 receive pins 40 of a glenoid positioner 42 (FIGS. 4 and 6) which is used to manipulate and position glenoid component 10 in the wound site when it is being implanted. Glenoid positioner 42 is also used to orient the humeral component 50 as will be explained later.

Figure 1:
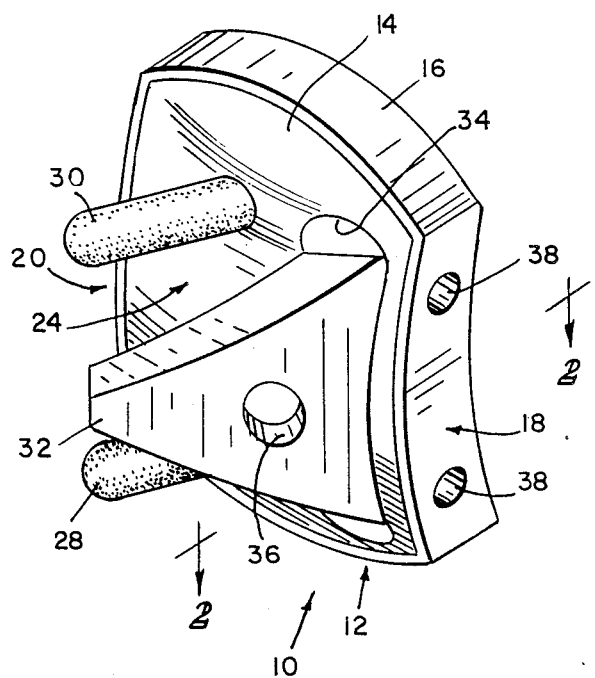
FIG. 1 is a perspective view of the glenoid component of this invention for an artificial shoulder joint from the scapular side of the glenoid component.
Figure 4:
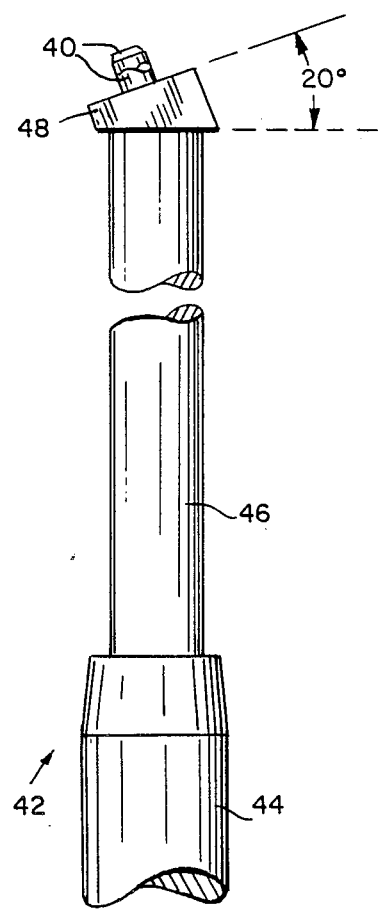
FIG. 4 is a perspective view of a glenoid positioner.
Figure 3:
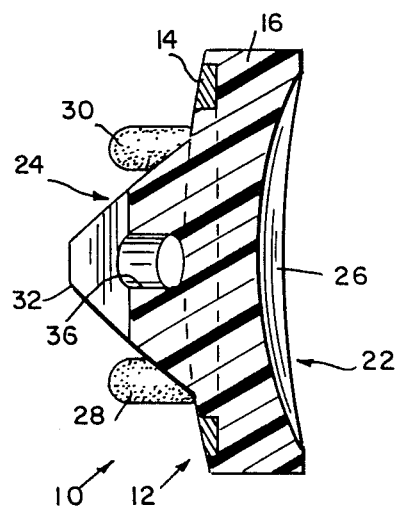
FIG. 3 is a section of the glenoid component of FIG. 2 taken along the line 3—3.
Figure 2:
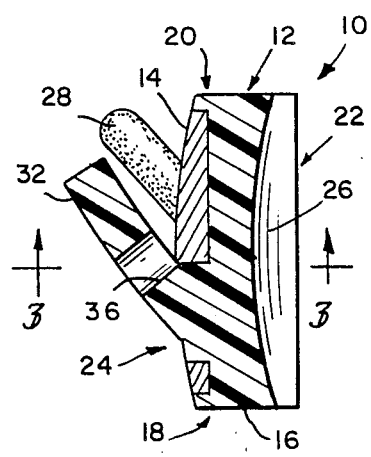
FIG. 2 is a section of the glenoid component of FIG. 1 taken along the line 2—2.

Referring to FIGS. 4 and 6, glenoid positioner 42 includes a handle 44 from which a shaft 46 extends. A T-head 48 is affixed to a distal end of shaft 46. Illustratively, T-head 48 is affixed to the distal end of shaft 46 at about a 20 degree angle thereto to alleviate interference between the glenoid positioner 42 and the patient's shoulder and to facilitate the use of the glenoid positioner 42. Pins 40 extend from opposite ends of T-head 48.

Referring to FIGS. 5 and 6, humeral component 50 includes a stem 52 having a distal end 54 and a proximal end 56. A tapered post 58 extends from proximal end 56 of humeral component 50 at an angle thereto. Stem 52 of humeral component 50 includes a plurality of fins 66, illustratively three, extending longitudinally therealong from the proximal end 56 of stem 52 part way down toward the distal end 54 of stem 52. Illustratively, fins 66 and tapered post 58 are equidistantly spaced around stem 52.

A hole 60 extends transversely through proximal end 56 of humeral component 50 generally where tapered post 58 joins proximal end 56 of humeral component 50. Hole 60 extends in a horizontal plane that is perpendicular to a vertical plane in which a centerline of stem 52 extends. In other words, if hole 60 intersected the centerline of stem 52, it would be perpendicular to the centerline of stem 52. Further, the horizontal plane in which hole 60 extends is also perpendicular to a vertical plane which extends through a centerline of the tapered post. In other words, if hole 60 intersected the centerline of tapered post 58, it would be perpendicular to the centerline of tapered post 58. Hole 60 receives a control wire 62 which is used in conjunction with glenoid positioner 42 to orient humeral component 50 to glenoid component 10. Control wire 62 is illustratively a stiff or rigid wire or a small diameter rigid rod.

After glenoid component 10 is affixed to the scapula of the shoulder, humeral component 50 is inserted into the humeral canal. Before this is done, humeral component 50 is oriented to glenoid component 10. Glenoid positioner 42 is reinserted into glenoid component 10 and control wire 62 is inserted into hole 60 of humeral component 50. Humeral component 50 is then oriented with respect to glenoid component 10 by initially driving the humeral component 50 into the humeral canal with the control wire 62 positioned at an angle twenty degrees to the handle 44 and shaft 46 of glenoid positioner 42. Once the fins 66 of humeral component 50 begin to cut into the humerus, the control wire 62 and the glenoid positioner 42 are removed and the stem 52 of the humeral component 50 fully seated. A ball 64 is then placed over tapered post 58 of humeral component 50. The use of glenoid positioner 42 and control wire 62 to orient the humeral component 50 to the glenoid component 10 provides the advantage of much more visible and easily used references to determine the orientation of humeral component 50 with respect to glenoid component 10.

It should be understood that the twenty degree angle between the control wire 62 and the handle 44 and shaft 46 of glenoid positioner 42 is to compensate for the twenty degree angle at which T-head 48 of glenoid positioner 42 is affixed to shaft 46. If T-head 48 was not affixed to shaft 46 at an angle, humeral component 50 would be oriented by positioning it so that control wire 62 would be parallel to handle 44 and shaft 46 of glenoid positioner 42.

Further, control wire 62 can also be used to orient humeral component 50 in situations where only humeral component 50 is to be implanted and used with the natural glenoid surface. In such cases, control wire 62 is inserted into hole 60 of humeral component 50. Humeral component 50 is then oriented by initially driving humeral component 50 into the humeral canal with control wire 62 positioned appropriately with respect to the natural glenoid surface and the forearm of the patient. Specifically, humeral component 50 is oriented by positioning control wire 62 in appropriate retroversion to the patient's forearm between ten and forty-five degrees therewith as determined by the anatomy of the patient. Similarly, humeral component 50 can be oriented with respect to glenoid component 10 without using glenoid positioner 42 by this procedure.

Although the invention has been described in detail with reference to certain preferred embodiments and specific examples, variations and modifications exist within the scope and spirit of the invention as described and as defined in the following claims.

What is claimed is:

1. In an artificial shoulder joint having a glenoid component and a humeral component, the glenoid component having a humerally facing concave articulating surface on which a ball of the humeral component articulates, an opposite scapular facing surface, a posterior side, a anterior side and at least one fixation member extending from the scapular facing surface outwardly towards the posterior side at an oblique angle to the scapular facing surface.

2. The glenoid component of claim 1 where the fixation member extends from the scapular facing surface of the glenoid component at an oblique angle to the articulating surface.

3. The glenoid component of claim 1 having a plurality of fixation members extending out from the scapular facing surface toward the posterior side of the glenoid component at an oblique angle to the articulating surface, at least one of the fixation members having a porous metal coating to promote bone ingrowth therein for long term fixation of the glenoid component to the scapula and at least one of the other fixation members comprising a plastic tab for being cemented to the scapula for short term fixation of the glenoid component to the scapula.

4. The glenoid component of claim 1 wherein the glenoid component comprises a porous metal coated retainer and an ultra high molecular weight polyethylene insert affixed to the retainer, the glenoid component affixed to the scapula with the retainer adjacent the scapula and the insert adjacent the humerus, the insert having a concave outer surface which comprises the concave articulating surface of the glenoid component, the glenoid component further including a plurality of fixation members wherein the retainer has a fixation member extending out from the scapular facing surface of the glenoid component toward the posterior side of the glenoid component at an oblique angle to the articulating surface, the retainer's fixation member comprising a porous metal coated post for promoting bone ingrowth therein for long-term fixation of the glenoid component to the scapula, the insert having a fixation member comprising a tab extending out from the scapular facing surface of the glenoid component through a slot in the retainer toward the posterior side at an oblique angle to the articulating surface for being cemented to the scapula for short-term fixation of the glenoid component to the scapula.

5. The glenoid component of claim 4 wherein the retainer has a plurality of porous metal posts extending out from the scapular facing surface of the glenoid component toward the posterior side of the glenoid component at an oblique angle to the articulating surface for long-term fixation of the glenoid component to the scapula, all the fixation members extending from the scapular facing, surface of the glenoid component at generally the same oblique angle to the articulating surface.

* * * * *